United States Patent
Nishibayashi et al.

(10) Patent No.: US 9,840,529 B2
(45) Date of Patent: Dec. 12, 2017

(54) HYDROGEN OXIDATION CATALYST

(71) Applicants: Yoshiaki Nishibayashi, Tokyo (JP); Masahiro Yuki, Tokyo (JP); Haruyuki Nakanishi, Susono (JP)

(72) Inventors: Yoshiaki Nishibayashi, Tokyo (JP); Masahiro Yuki, Tokyo (JP); Haruyuki Nakanishi, Susono (JP)

(73) Assignees: THE UNIVERSITY OF TOKYO, Tokyo (JP); TOYOTA JIDOSHA KABUSHIKI KAISHA, Toyota (JP)

(*) Notice: Subject to any disclaimer, the term of this patent is extended or adjusted under 35 U.S.C. 154(b) by 0 days.

(21) Appl. No.: 15/037,824

(22) PCT Filed: Oct. 14, 2014

(86) PCT No.: PCT/JP2014/077333
§ 371 (c)(1),
(2) Date: May 19, 2016

(87) PCT Pub. No.: WO2015/076038
PCT Pub. Date: May 28, 2015

(65) Prior Publication Data
US 2016/0289254 A1 Oct. 6, 2016

(30) Foreign Application Priority Data

Nov. 20, 2013 (JP) ................. 2013-239924

(51) Int. Cl.
| C07F 15/00 | (2006.01) |
| C07F 17/02 | (2006.01) |
| B01J 31/22 | (2006.01) |
| C07C 309/06 | (2006.01) |
| H01M 4/90 | (2006.01) |
| H01M 8/18 | (2006.01) |
| H01M 8/20 | (2006.01) |
| H01M 4/86 | (2006.01) |

(52) U.S. Cl.
CPC .............. C07F 17/02 (2013.01); B01J 31/22 (2013.01); C07C 309/06 (2013.01); H01M 4/9008 (2013.01); H01M 8/188 (2013.01); H01M 8/20 (2013.01); *H01M 2004/8684* (2013.01)

(58) Field of Classification Search
CPC ..... C07F 17/02; H01M 4/9008; H01M 8/188; H01M 8/20; B01J 31/22; C07C 309/06
USPC .......................................................... 556/14
See application file for complete search history.

(56) References Cited

FOREIGN PATENT DOCUMENTS

JP     2009-289681 A    12/2009

OTHER PUBLICATIONS

Yuki et al., Organometallics 2010, 29, 5994-6001.*
Yuki, Masahiro et al. "Preparation of Thiolate-Bridged Dinuclear Ruthenium Complexes Bearing a Phosphine Ligand and Application to Propargylic Reduction of Propargylic Alcohols With 2-Propanol". Organometallics, vol. 29, No. 22, 2010, pp. 5994-6001.

* cited by examiner

*Primary Examiner* — Fereydoun G Sajjadi
*Assistant Examiner* — Kofi Adzamli
(74) *Attorney, Agent, or Firm* — Oliff PLC

(57) ABSTRACT

The present invention is to provide a hydrogen oxidation catalyst that does not contain platinum. Disclosed is a hydrogen oxidation catalyst that is a dinuclear transition metal complex having a chemical structure represented by the following general formula (1) or (2):

General Formula (1)

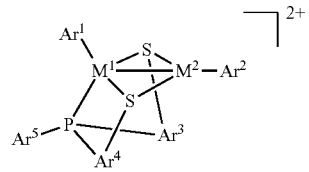

General Formula (2)

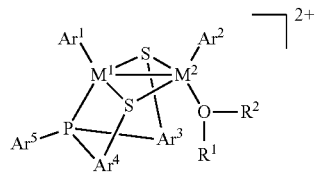

wherein, in the general formulae (1) and (2), $M^1$ and $M^2$ are each independently Fe or Ru; $Ar^1$ and $Ar^2$ are each independently a cyclopentadienyl group or a pentamethylcyclopentadienyl group; $Ar^3$ and $Ar^4$ are each independently a divalent aromatic hydrocarbon group having 6 to 12 carbon atoms; and $Ar^5$ is a monovalent aromatic hydrocarbon group having 6 to 12 carbon atoms, and in the general formula (2), $R^1$ and $R^2$ are each independently a hydrogen atom or a monovalent aliphatic hydrocarbon group having 1 to 3 carbon atoms.

2 Claims, 1 Drawing Sheet

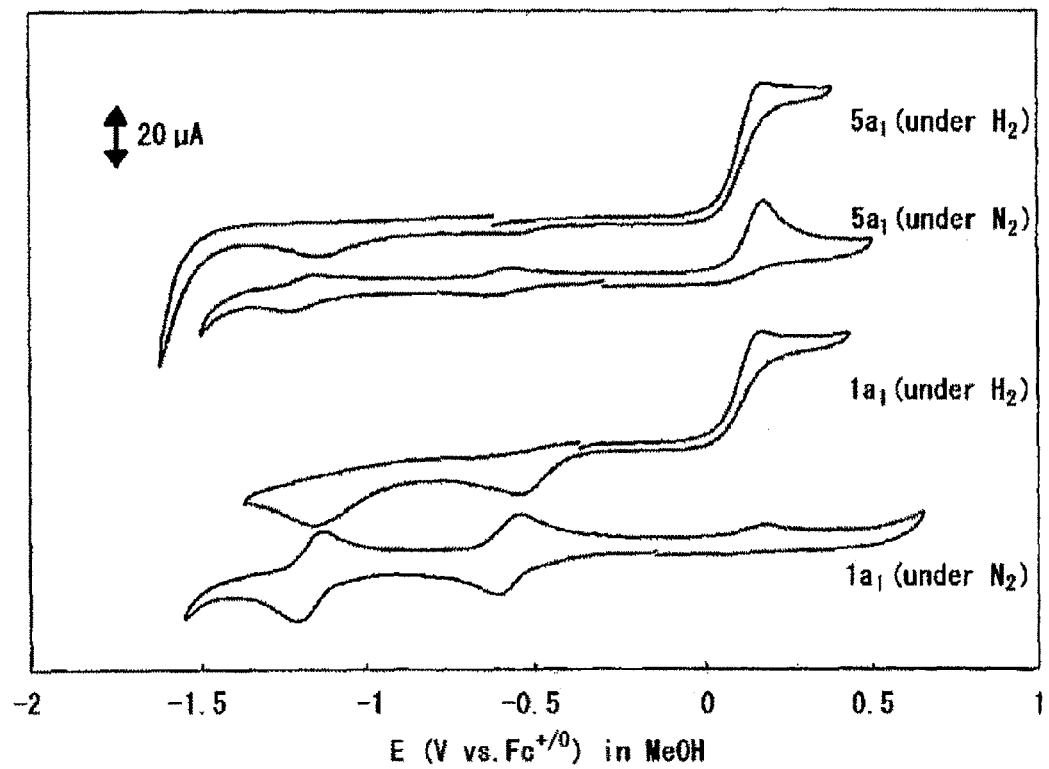

HYDROGEN OXIDATION CATALYST

TECHNICAL FIELD

The present invention relates to a hydrogen oxidation catalyst that does not contain platinum.

BACKGROUND ART

Platinum catalyst is widely used as fuel cell anode catalyst (Patent Literature 1). Platinum catalyst has excellent hydrogen oxidizing ability. However, since platinum, which is a raw material therefor, is expensive and rare, there is a demand for less expensive hydrogen oxidation catalyst, as fuel cell anode catalyst.

Meanwhile, an example if described in Non-Patent Literature 1, in which a thiolate-bridged ruthenium dinuclear complex is used for propargyl alcohol reduction.

CITATION LIST

Patent Literature 1: Japanese Patent Application Laid-Open No. 2009-289681
Non-Patent Literature 1: Organometallics 2010, 29, 5994-6001

SUMMARY OF INVENTION

Technical Problem

There has been considerable research on hydrogen oxidation catalysts that have excellent hydrogen oxidizing ability and are inexpensive. However, practical examples of hydrogen oxidation catalysts that do not contain platinum, are not found yet.

The present invention was achieved in light of such a circumstance that low-cost hydrogen oxidation methods have been sought. The object of the present invention is to provide a hydrogen oxidation catalyst that does not contain platinum.

Solution to Problem

The hydrogen oxidation catalyst of the present invention is a dinuclear transition metal complex having a chemical structure represented by the following general formula (1) or (2):

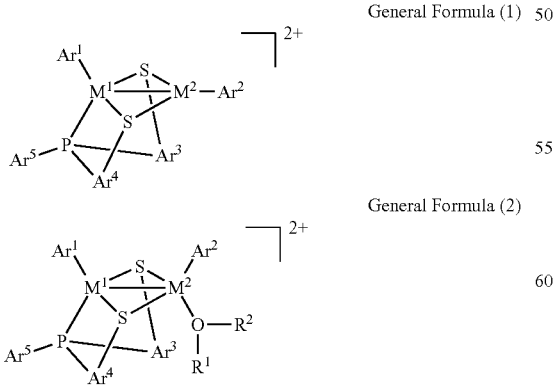

wherein, in the general formulae (1) and (2), $M^1$ and $M^2$ are each independently Fe or Ru; $Ar^1$ and $Ar^2$ are each independently a cyclopentadienyl group or a pentamethylcyclopentadienyl group; $Ar^3$ and $Ar^4$ are each independently a divalent aromatic hydrocarbon group having 6 to 12 carbon atoms; and $Ar^5$ is a monovalent aromatic hydrocarbon group having 6 to 12 carbon atoms, and in the general formula (2), $R^1$ and $R^2$ are each independently a hydrogen atom or a monovalent aliphatic hydrocarbon group having 1 to 3 carbon atoms.

Advantageous Effects of Invention

According to the present invention, any of the dinuclear transition metal complexes represented by the general formulae (1) and (2) has excellent hydrogen oxidizing ability; therefore, a highly-efficient, hydrogen oxidation catalyst reaction can be realized without the use of platinum.

BRIEF DESCRIPTION OF DRAWING

FIG. 1 is a graph showing cyclic voltammograms of a complex $1a_1$ and a hydride complex $5a_1$ under hydrogen atmosphere or nitrogen atmosphere, the voltammograms being arranged side by side.

DESCRIPTION OF EMBODIMENTS

The hydrogen oxidation catalyst of the present invention is a dinuclear transition metal complex having a chemical structure represented by the following general formula (1) or (2):

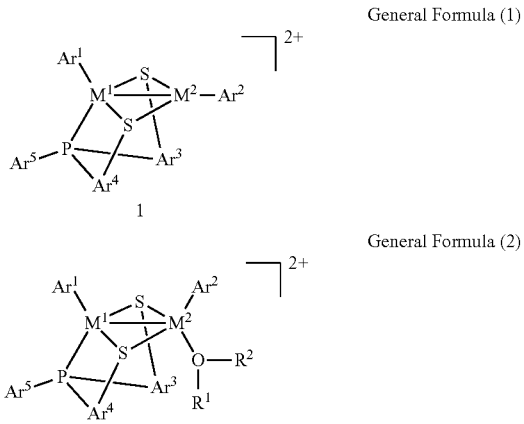

wherein, in the general formulae (1) and (2), $M^1$ and $M^2$ are each independently Fe or Ru; $Ar^1$ and $Ar^2$ are each independently a cyclopentadienyl group or a pentamethylcyclopentadienyl group; $Ar^3$ and $Ar^4$ are each independently a divalent aromatic hydrocarbon group having 6 to 12 carbon atoms; and $Ar^5$ is a monovalent aromatic hydrocarbon group having 6 to 12 carbon atoms, and in the general formula (2), $R^1$ and $R^2$ are each independently a hydrogen atom or a monovalent aliphatic hydrocarbon group having 1 to 3 carbon atoms.

Any of the divalent cation complex represented by the general formula (1) (hereinafter it may be referred to as complex 1) and the divalent cation complex represented by the general formula (2) (hereinafter it may be referred to as complex 2) is a complex that contains two transition metal atoms. The complex 2 has the same chemical structure as the complex 1, except that a ligand $R^1OR^2$ is coordinated to $M^2$, which is a transition metal element.

Hereinafter, the chemical structure which is common to the complexes 1 and 2 will be described.

Any of the complexes 1 and 2 has the transition metal elements $M^1$ and $M^2$. These $M^1$ and $M^2$ are each independently iron or ruthenium. For example, both $M^1$ and $M^2$ can be ruthenium; $M^1$ can be iron and $M^2$ can be ruthenium; $M^1$ can be ruthenium and $M^2$ can be iron; or both $M^1$ and $M^2$ can be iron. Among these examples, it is preferred that both $M^1$ and $M^2$ are ruthenium, or that $M^1$ is iron and $M^2$ is ruthenium. It is more preferred that both $M^1$ and $M^2$ are ruthenium. It is considered that the use of a ruthenium or iron element that is likely to form a molecular hydrogen complex which is expected to be a key intermediate of reaction, has a positive effect on hydrogen oxidation reaction.

The transition metal elements $M^1$ and $M^2$ are bound to each other by a single bond; moreover, they have two cross-linked structures by a sulfur atom. In addition, a phosphorus atom is coordinated to the transition metal element $M^1$.

The complexes 1 and 2 have aromatic hydrocarbon groups $Ar^1$ to $Ar^5$. Among the aromatic hydrocarbon groups, $Ar^1$ and $Ar^2$ are directly coordinated to $M^1$ or $M^2$ and are each independently a cyclopentadienyl group (Cp) or a pentamethylcyclopentadienyl group (Cp*). For example, both $Ar^1$ and $Ar^2$ can be pentamethylcyclopentadienyl groups; $Ar^1$ can be a cyclopentadienyl group and $Ar^2$ can be a pentamethylcyclopentadienyl group; $Ar^1$ can be a pentamethylcyclopentadienyl group and $Ar^2$ can be a cyclopentadienyl group; or both $Ar^1$ and $Ar^2$ can be cyclopentadienyl groups. Among them, it is preferred that both $Ar^1$ and $Ar^2$ are pentamethylcyclopentadienyl groups, or that $Ar^1$ is a cyclopentadienyl group and $Ar^2$ is a pentamethylcyclopentadienyl group. It is more preferable that both $Ar^1$ and $Ar^2$ are pentamethylcyclopentadienyl groups. Cyclopentadienyl groups and pentamethylcyclopentadienyl groups serve effectively as electron donating groups, with respect to core metal (coordination metal). Moreover, they are effective in stabilizing core metal-containing complexes.

$Ar^3$ and $Ar^4$ are divalent aromatic hydrocarbon groups having 6 to 12 carbon atoms. $Ar^3$ and $Ar^4$ can be groups that are the same as or different from each other.

$Ar^3$ and $Ar^4$ are not particularly limited, as long as they are arylene groups having the same number of carbon atoms as above. Examples thereof include phenylene group ($—C_6H_4—$), tolylene group ($—C_6H_3CH_3—$), naphthylene group ($—C_{10}H_6—$) and biphenylene group ($—C_{12}H_8—$). Among them, phenylene group is preferred, and 1,2-phenylene group is more preferred.

$Ar^5$ is a monovalent aromatic hydrocarbon group having 6 to 12 carbon atoms. $Ar^5$ is not particularly limited, as long as it is an aryl group having 6 to 12 carbon atoms. Examples thereof include phenyl group ($—C_6H_5$), tolyl group ($—C_6H_4CH_3$), benzyl group ($—CH_2C_6H_5$), xylyl group ($—C_6H_3(CH_3)_2$), mesityl group ($—C_6H_2(CH_3)_3$), naphthyl group ($—C_{10}H_7$) and biphenyl group ($—C_{12}H_9$). Among them, phenyl group, tolyl group, xylyl group and mesityl group are preferred, and phenyl group is more preferred.

Hereinafter, the ligand $R^1OR^2$ in the complex 2 will be described.

In the general formula (2), $R^1$ and $R^2$ are a hydrogen atom or a monovalent aliphatic hydrocarbon group having 1 to 3 carbon atoms. That is, the ligand $R^1OR^2$ is water, alcohol or ether.

$R^1$ and $R^2$ can be groups that are the same as or different from each other. Examples of $R^1$ and $R^2$ include hydrogen atom, methyl group, ethyl group, n-propyl group and i-propyl group. Among them, hydrogen atom and methyl group are preferred. It is more preferred that both $R^1$ and $R^2$ are hydrogen atoms, that is, the ligand $R^1OR^2$ is water ($H_2O$).

The hydrogen oxidation catalyst of the present invention can appropriately have an anion. Examples of the anion include trifluoromethanesulfonic acid anion ($CF_3SO_3^-$), hexafluorophosphoric acid anion ($PF_6^-$), tetrafluoroboric acid anion ($BF_4^-$), and tetrakis[3,5-bis(trifluoromethyl)phenyl]boric acid anion ($^-B(C_6H_3(CF_3)_2)_4=^-BAr^F_4$). Among these anions, trifluoromethanesulfonic acid anion is preferred.

As for the method for producing the hydrogen oxidation catalyst of the present invention, an example is described in the above-mentioned Non-Patent Literature 1 (Organometallics 2010, 29, 5994-6001).

A typical example of the method for producing the hydrogen oxidation catalyst of the present invention is a production method based on a two-step reaction, as described in Non-Patent Literature 1.

The first step of the production method is the synthesis of a mononuclear complex $[Ar^1M^1\{Ar^5P(Ar^3S)(Ar^4S)\}]$ in which the transition metal element $M^1$ is contained (a complex 4 in the following formula (3)). First, as shown in the following formula (3), a phosphorus sulfur ligand $Ar^5P(Ar^3SH)(Ar^4SH)$ (a compound 3 in the following formula (3)) is exposed to the action of base. Then, the phosphorus sulfur ligand is reacted with a metal complex that contains $Ar^1M^1$ ($[Ar^1M^1]$ in the formula (3)), thereby synthesizing $[Ar^1M^1\{Ar^5P(Ar^3S)(Ar^4S)\}]$.

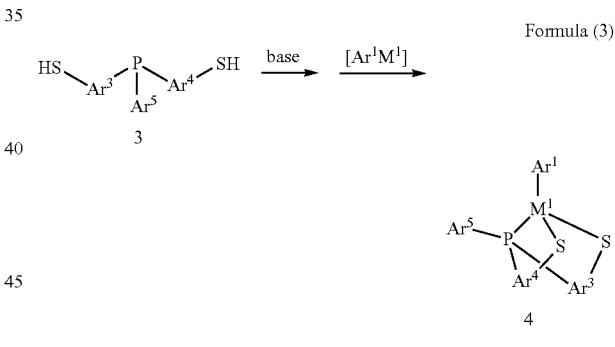

In the second step of the production method, as shown in the following formula (4), $[Ar^1M^1\{Ar^5P(Ar^3S)(Ar^4S)\}]$ (the complex 4) is mixed and reacted with a metal complex that contains $Ar^2M^2$ ($[Ar^2M^2]$ in the following formula (4)), thereby obtaining the target complex 1 or 2. To obtain a stable complex, anion exchange or the like can be appropriately carried out after the reaction of the complex 4 with $[Ar^2M^2]$.

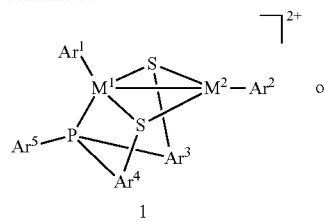

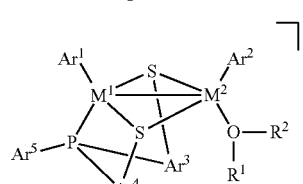

As will be shown below under "Examples", the estimated reaction mechanism of the hydrogen oxidation catalyst reaction developed by the hydrogen oxidation catalyst of the present invention, is as shown in the following formula (5).

As shown in the following formula (5), by the reaction of the complex 1 (divalent cation) with hydrogen, a complex 5 (monovalent cation) is produced with the production of one equivalent of protons. By the oxidation of the complex 5, the complex 1 is regained with the production of another one equivalent of protons. Detailed analysis of the reaction mechanism will be described below under "Examples".

In the case of the complex 2, it is predicted that after the complex 2 becomes the complex 5 through the desorption of the ligand $R^1OR^2$ from the complex 2 and the coordination of hydrogen ($H_2$) to the metal $M^2$, a similar catalyst cycle to the following formula (5) proceeds:

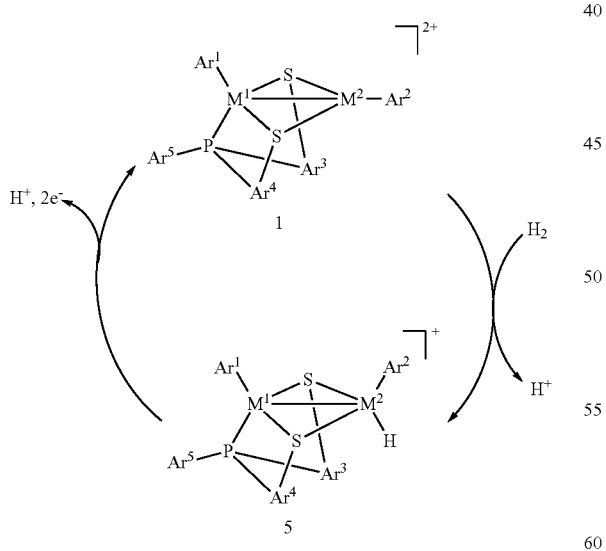

Formula (5)

The hydrogen oxidation method using the hydrogen oxidation catalyst of the present invention is not particularly limited. Examples thereof include a method in which the hydrogen oxidation catalyst of the present invention is dissolved in a solvent to obtain a solution, and the solution is oxidized by bubbling hydrogen thereinto.

The condition of the hydrogen oxidation method using the hydrogen oxidation catalyst of the present invention, is not particularly limited. Examples thereof include a condition in which hydrogen pressure is set to 0.01 to 100 atm, and 0.01 to 10 mmol of the hydrogen oxidation catalyst of the present invention is used.

The hydrogen oxidation catalyst of the present invention is widely applicable to all the technology fields which require hydrogen oxidation. Examples of the applications of the hydrogen oxidation catalyst of the present invention, include an anode catalyst for fuel cells in which hydrogen is used as fuel, and an anode catalyst for redox flow batteries. Especially in redox flow batteries, which have been growing in size, the hydrogen oxidation catalyst having high catalytic efficiency and being less expensive than conventional platinum catalysts, like the present invention, is useful as a cost minimization technique.

EXAMPLES

Hereinafter, the present invention will be described in more detail, by way of examples and comparative examples. The scope of the present invention is not limited to the examples.

1. Production of Hydrogen Oxidation Catalyst

The hydrogen oxidation catalyst production method used below is based on the method for producing compounds 4a, 4b and 4c described in the above-mentioned Non-Patent Literature 1 (Organometallics 2010, 29, 5994-6001).

Example 1

(1) Synthesis of [Cp*Ru{PhP($C_6H_4$-o-S)$_2$}] (the following formula (6a))

First, under a temperature condition of 0° C., n-butyllithium (1.57 M hexane solution, 2.60 mL, 4.08 mmol) was added to 20 mL of a THF solution of [PhP($C_6H_4$-o-SH)$_2$] (653 mg, 2.00 mmol). Fifteen minutes after the addition, at room temperature, a yellow solution thus obtained was added to 10 mL of a THF dispersion of [Cp*RuCl(μ-Cl)]$_2$ (609 mg, 0.991 mmol). A mixture thus obtained was stirred for 18 hours at room temperature. A violet solution thus obtained was concentrated and dried, thereby obtaining a violet solid. By recrystallization using methylene-chloride-hexane, a violet needle crystal ([Cp*Ru{PhP($C_6H_4$-o-S)$_2$}].0.5$CH_2Cl_2$) was obtained (916 mg, 1.52 mmol, 77%). Anal. Calcd for $C_{28}H_{28}PRuS_2$: C, 59.98; H, 5.03. Found: C, 60.24; H, 4.84.

Formula (6a)

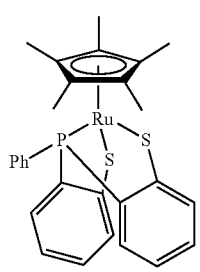

(2) Synthesis of [Cp*Ru{PhP($C_6H_4$-o-S)$_2$}RuCp*] (OTf)$_2$ (the following formula (1a))

A mixture of the above-mentioned [Cp*Ru{PhP($C_6H_4$-o-S)$_2$}] (114 mg, 0.203 mmol) and 10 mL of a methylene chloride solution of [Cp*RuCl(μ-Cl)]₂ (60.4 mg, 0.0983 mmol) was mixed for 20 hours at room temperature. To a solution thus obtained, silver trifluoromethanesulfonate (AgOTf, 113 mg, 0.438 mmol) was added. A mixture thus obtained was further stirred for one hour at room temperature. A reaction mixture thus obtained was filtered and concentrated. In addition, by a first recrystallization using ethanol-ether and a second recrystallization using methylene chloride-hexane, a crystalline solid ([Cp*Ru{PhP(C₆H₄-o-S)₂}RuCp*](OTf)₂.0.5CH₂Cl₂) was obtained (186 mg, 0.164 mmol, 83%). ¹HNMR (CD₂Cl₂): δ8.45 (dd, J=8 and 2 Hz, 2H), 7.92-7.83 (m, 2H). 7.69-7.45 (m, 7H), 6.84-6.75 (m, 2H), 1.70 (d, J=2 Hz, 15H), 1.48 (s, 15H).
³¹P{¹H}NMR(CD₂Cl₂): δ94.8 (s).

Anal. Calcd for C₄₀.₅H₄₄ClF₆O₆PRu₂S₄([Cp*Ru{PhP(C₆H₄-o-S)₂}RuCp*](OTf)₂.0.5CH₂Cl₂): C, 42.76; H, 3.90. Found: C, 42.89; H, 3.74.

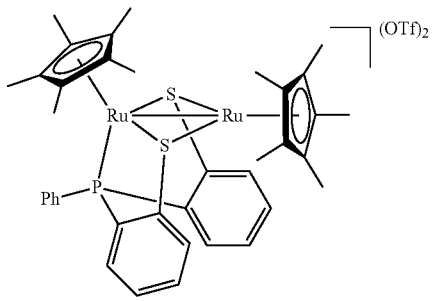

Formula (1a)

Example 2

(1) Synthesis of [CpRu{PhP(C₆H₄-o-S)₂}] (the following formula (6b))

First, under a temperature condition of 0° C., n-butyllithium (1.65 M hexane solution, 0.60 mL, 0.990 mmol) was added to 15 mL of a THF solution of [PhP(C₆H₄-o-SH)₂] (163 mg, 0.498 mmol). Thirty minutes after the addition, at room temperature, a yellow solution thus obtained was added to 10 mL of a THF solution of [CpRu(NCMe)₃]PF₆ (219 mg, 0.504 mmol). A red-brown solution thus obtained was stirred for 18 hours at room temperature. The stirred solution was oxidized with air for three hours, thereby obtaining an orange-brown solution. The orange-brown solution was concentrated under a reduced pressure condition. A product thus obtained was purified by passing the product through a silica gel pad, using methylene chloride as a mobile phase. By recrystallization using THF-hexane, a black rectangular crystal ([CpRu{PhP(C₆H₄-o-S)₂}].0.5C₆H₁₄) was obtained (182 mg, 0.341 mmol, 68%).

Anal. Calcd for C₂₃H₁₈PRuS₂: C, 56.31; H, 3.70. Found: C, 56.13; H, 3.89.

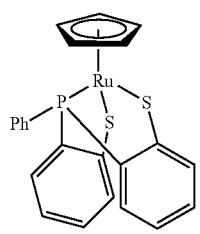

Formula (6b)

(2) Synthesis of [CpRu{PhP(C₆H₄-o-S)₂}RuCp*(OH₂)](OTf)₂ (the following formula (2a))

A mixture of the above-mentioned [CpRu{PhP(C₆H₄-o-S)₂}] (50.0 mg, 0.102 mmol) and 5 mL of a methylene chloride solution of [Cp*RuCl(μ-Cl)]2 (30.0 mg, 0.0488 mmol) was mixed for 20 hours at room temperature. To a solution thus obtained, silver trifluoromethanesulfonate (AgOTf, 55.6 mg, 0.216 mmol) was added. A mixture thus obtained was further stirred for one hour at room temperature. A reaction mixture thus obtained was filtered and concentrated. In addition, by recrystallization using methylene chloride-hexane, a green crystalline solid ([CpRu{PhP(C₆H₄-o-S)₂}RuCp*(OH₂)](OTf)₂.0.5 CH₂Cl₂) was obtained (87.4 mg, 0.0805 mmol, 82%). ¹HNMR (CD₂Cl₂): δ7.94 (dd, J=8 and 2 Hz, 2H), 7.68-7.45 (m, 9H), 7.23 (dd, J=13 and 7 Hz, 2H), 5.37 (s, 5H), 1.77 (s, 15H). ³¹P{¹H}NMR(CD₂Cl₂): δ103.1 (s).

Anal. Calcd for C₃₅.₅H₃₆ClF₆O₇PRu₂S₄ ([CpRu{PhP(C₆H₄-o-S)₂}RuCp*(OH₂)](OTf)₂.0.5CH₂Cl₂) C, 39.28; H, 3.34. Found: C, 39.20; H, 3.27.

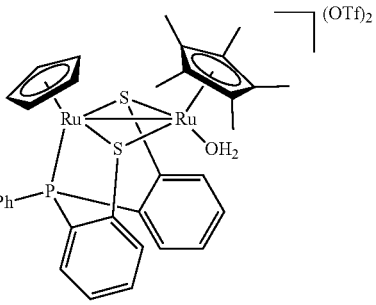

Formula (2a)

Example 3

(1) Synthesis of [Cp*Fe{PhP(C₆H₄-o-S)₂}] (the following formula (6c))

First, under a temperature condition of 0° C., n-butyllithium (1.57 M hexane solution, 1.28 mL, 2.01 mmol) was added to 20 mL of a THF solution of [PhP(C₆H₄-o-SH)₂] (326 mg, 1.00 mmol). Fifteen minutes after the addition, a yellow solution thus obtained was moved to a container containing 10 mL of a THF solution of [Cp*FeCl(tmeda)] (343 mg, 1.00 mmol). A mixture thus obtained was stirred for 18 hours at room temperature. After the stirring, a black-green solution thus obtained was exposed to air and vigorously stirred for one hour. The color of the solution quickly changed to violet. A product thus obtained was purified by passing the product through a silica gel pad, using methylene chloride as a mobile phase. By recrystallization using methylene chloride-hexane, a violet needle crystal ([Cp*Fe{PhP(C₆H₄-o-S)₂}]) was obtained (382 mg, 0.741 mmol, 74%).

Anal. Calcd for C₂₈H₂₈FePS₂: C, 65.24; H, 5.48. Found: C, 65.13; H, 5.43.

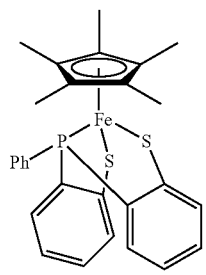

Formula (6c)

(2) Synthesis of [Cp*Fe{PhP(C₆H₄-o-S)₂}RuCp*](OTf)₂ (the following formula (1b))

A mixture of the above-mentioned [Cp*Fe{PhP(C₆H₄-o-S)₂}] (111 mg, 0.216 mmol) and 10 mL of a methylene chloride solution of [Cp*RuCl(μ-Cl)]2 (61.0 mg, 0.0993 mmol) was mixed for 20 hours at room temperature. To a solution thus obtained, silver trifluoromethanesulfonate (AgOTf, 110 mg, 0.428 mmol) was added. A mixture thus obtained was further stirred for one hour at room temperature. A reaction mixture thus obtained was filtered and concentrated. In addition, by a first recrystallization using ethanol-ether and a second crystallization using methylene chloride-hexane, a green crystalline solid ([Cp*Fe{PhP(C₆H₄-o-S)₂}RuCp*](OTf)₂.0.5CH₂Cl₂) was obtained (167 mg, 0.153 mmol, 77%). $^1$HNMR (CD₂Cl₂): δ8.47 (dd, J=8 and 2 Hz, 2H), 7.92-7.8 (m, 2H), 7.67-7.40 (m, 7H), 6.80-6.69 (m, 2H), 1.60 (s, 15H), 1.45 (s, 15H).

$^{31}$P{$^1$H}NMR (CD₂Cl₂): δ110.9 (s).

Anal. Calcd for C₄₀.₅H₄₄ClF₆FeO₆PRuS₄ ([Cp*Fe{PhP(C₆H₄-o-S)₂}RuCp](OTf)₂.0.5CH₂Cl₂): C, 44.53; H, 4.06. Found: C, 44.55; H, 3.88.

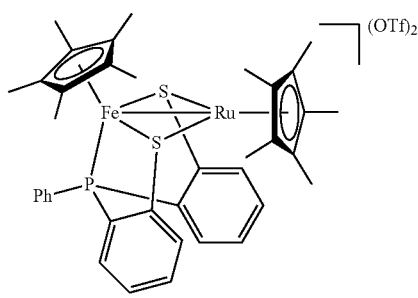

Formula (1a)

2. Evaluation of Hydrogen Oxidation Catalyst
(1) Evaluation of Hydrogen Oxidation Reaction A hydrogen oxidation reaction was developed using the hydrogen oxidation catalyst of Example 1 ([Cp*Ru{PhP(C₆H₄-o-S)₂}RuCp*](OTf)₂; hereinafter it may be referred to as complex 1a₁). [Cp₂Fe]OTf was used as an oxidant.

First, as shown in the following formula (7), [Cp₂Fe]OTf (0.4 mmol) and the complex 1a₁ (5 mol %) were dissolved in 5 mL of water. Under a room temperature condition, an aqueous solution thus obtained was reacted by supplying one atmosphere of hydrogen for 20 hours to the solution. As a result, with respect to [Cp₂Fe]OTf (0.4 mmol), HOTf and Cp₂Fe were obtained at yields of 86% and 87%, respectively. The raw material [Cp₂Fe]OTf was not obtained.

Next, as shown in the following formula (8), under a room temperature condition, an aqueous solution of a mixture of [Cp₂Fe]OTf (0.4 mmol) and the complex 1a₁ (5 mol %) was reacted by supplying one atmosphere of nitrogen for 20 hours to the solution. A solution thus obtained was still dark blue, which is a color that is derived the raw material [Cp₂Fe]OTf, even after 20 hours. A precipitate thus obtained was extracted with hexane; therefore, Cp₂Fe was obtained at a yield of 18%. After the extraction with hexane, an aqueous phase thus obtained was washed with dichloromethane and then subjected to UV measurement to quantitate the raw material [Cp₂Fe]OTf. As a result, a raw material collection rate of 62% was obtained. HOTf was not obtained.

Then, as shown in the following formula (9), under a room temperature condition, an aqueous solution of [Cp₂Fe]OTf (0.4 mmol) was reacted by supplying one atmosphere of hydrogen for 20 hours to the solution. As a result, with respect to [Cp₂Fe]OTf (0.4 mmol), Cp₂Fe was obtained at a yield of 19%, and a raw material collection rate of 57% was obtained. HOTf was not obtained.

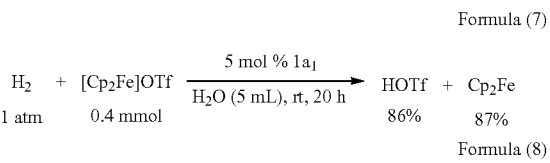

Formula (7)

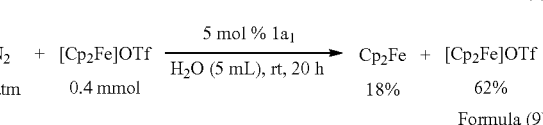

Formula (8)

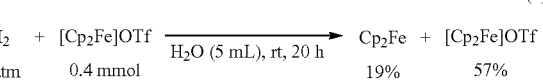

Formula (9)

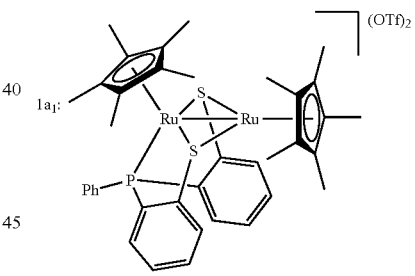

From the above results, it is clear that under any reaction condition, [Cp₂Fe]OTf is partially decomposed and Cp₂Fe (ferrocene) is obtained. However, from the result that [Cp₂Fe]OTf was absolutely consumed under the reaction condition of the formula (7), it was confirmed that oxidation reaction of hydrogen molecules is catalytically promoted by the complex 1a₁. The aqueous solution of [Cp₂Fe]OTf was still dark blue, even after it was left to stand for about one month, and [Cp₂Fe]OTf was not absolutely decomposed.

(2) NMR Experiment

Next, to obtain information on ruthenium species which are produced under hydrogen atmosphere, an NMR experiment was carried out.

First, as shown in the following formula (10), the complex 1a₁ was dissolved in methylene chloride-d₂ to obtain a solution. Hydrogen gas was bubbled into the solution. As a result, almost no change was observed in the solution.

Next, as shown in the following formula (11), the complex 1a₁ (one equivalent) and lutidine (base, 5 equivalent)

were dissolved in methylene chloride-$d_2$ to obtain a solution. Hydrogen gas was bubbled into the solution. As a result, the color of a reaction solution thus obtained changed from green to orange-brown in several minutes.

As a result of measuring the $^1$HNMR of the reaction solution, the peak which is assigned to the complex $1a_1$ disappeared absolutely, and only the peak which is assigned to a hydride complex $5a_1$ was observed. In the $^1$HNMR of the hydride complex $5a_1$, the peak which is characteristic of hydride ligand (–H$^-$) appears in a high magnetic field of –16.4 ppm. No dihydrogen complex intermediate was obtained, in which hydrogen (H$_2$) is coordinated to ruthenium.

Meanwhile, it was found that the hydride complex $5a_1$ is produced by exposing a methanol solution of the complex $1a_1$ to hydrogen. It is considered that in this reaction, the methanol itself serves as base. As shown in the following formula (12), a yellow-brown powder was obtained by adding one equivalent of KOtBu to a methanol solution of the hydride complex $5a_1$ obtained, reacting the mixture for 20 minutes, and then drying the resultant. The yellow-brown powder contained about 80% of the hydride complex $5a_1$ and about 20% of the complex $1a_1$.

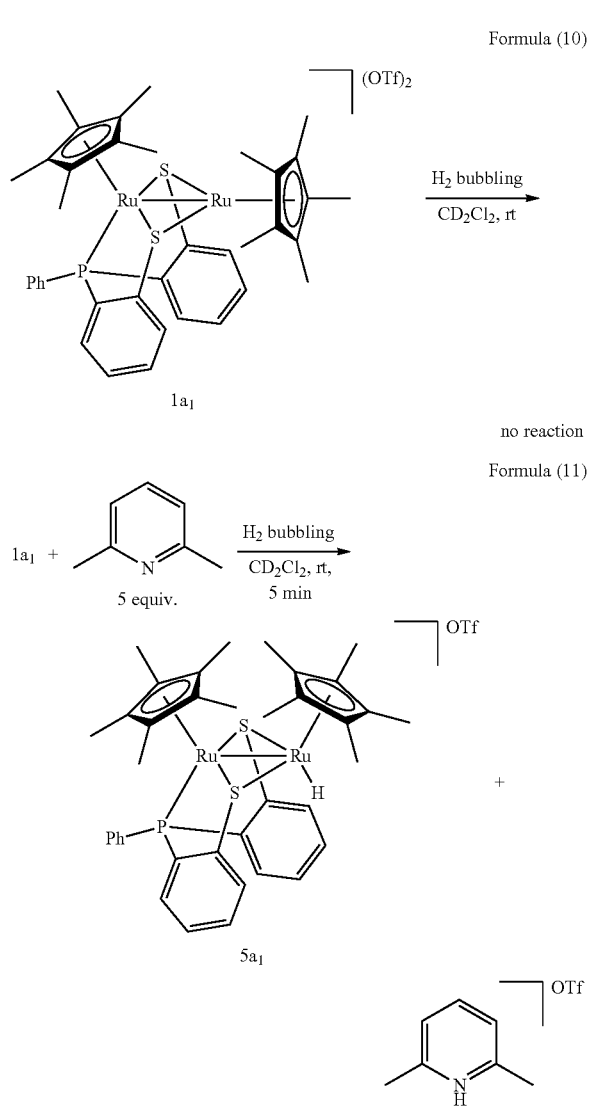

Formula (10)

Formula (11)

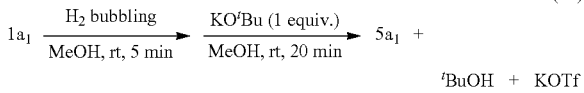

Formula (12)

The methylene chloride-$d_2$ was removed from the reacted solution shown in the above formula (11). As a result of drying the solution, a solid thus obtained became a mixture that contains the complex $1a_1$ as a main component. From this result, it is clear that the reaction shown in the formula (11) is an equilibrium reaction (the following formula (13)). Also in acetone-$d_6$, almost the same result as the formulae (10) and (11) was obtained.

From the formulae (10) to (12), it is clear that the hydride complex $5a_1$ is produced by exposing the complex $1a_1$ to hydrogen. In the formulae (10) to (12), particularly no reaction proceeds after the production of the hydride complex $5a_1$.

Therefore, the next step in the catalyst reaction is considered to be the oxidation reaction of the hydride complex $5a_1$ (the following formula (14)).

$$1a_1 + H_2 \rightleftharpoons 5a_1 + HOTf$$ Formula (13)

$$5a_1 + HOTf \longrightarrow 1a_1 + H_2$$ Formula (14)

(3) Cyclic Voltammetry

Next, to clarify the oxidation-reduction behavior of the complex $1a_1$ and the hydride complex $5a_1$, cyclic voltammetry (CV) was carried out. Details of the measurement cell and measurement conditions used for the CV are as follows.

Measurement Cell
  Working electrode: Glassy carbon electrode
  Reference electrode: Platinum quasi-reference electrode (Pt-QRE)
  Counter electrode: Platinum electrode
  Sample solution: Methanol solution of the complex $1a_1$ or the hydride complex $5a_1$ ($^n$Bu$_4$NClO$_4$ and ferrocene were added as supporting electrolyte and internal standard, respectively)
  Measurement device: Potentiostat/galvanostat (Solatron)
  Potential sweep rate: 50 mV/sec
  Potential sweep range: –1.7 to 0.7 V (vs. Fc/Fc$^+$)
  Measurement temperature: 25° C.
  Measurement atmosphere: Nitrogen atmosphere or hydrogen atmosphere It is known that the complex $1a_1$ quickly reacts with coordinating solvents such as acetonitrile, halide ions, etc. Accordingly, these coordinating solvents and halide ions cannot be used for CV. $^n$Bu$_4$NClO$_4$ was used as supporting electrolyte since $^n$Bu$_4$NBF$_4$, etc., could not be used. Also, the platinum quasi-reference electrode (Pt-QRE) was used since Ag/AgNO$_3$-MeCN, Ag/AgCl-KClaq, etc., which are generally used as working electrode, could not be used. Also, ferrocene was added as internal standard, and the oxidation-reduction potential of ferrocene was used as standard potential.

The complex $1a_1$ was dissolved in methanol. Also, the hydride complex $5a_1$ (actually, a mixture containing about 20% of the complex $1a_1$) was dissolved in methanol. CV was carried on each solution, under hydrogen atmosphere or nitrogen atmosphere. FIG. 1 is a graph showing cyclic voltammograms of the complex $1a_1$ and the hydride complex $5a_1$ under hydrogen atmosphere or nitrogen atmosphere, the voltammograms being arranged side by side.

The cyclic voltammogram of the complex $1a_1$ in the methanol and under the nitrogen atmosphere (the first voltammogram from the bottom in FIG. 1) showed a reversible one-electron reduction wave at −587 mV (vs. Fc/Fc⁺) and −1180 mV (vs. Fc/Fc⁺). Meanwhile, in the cyclic voltammogram of the complex $1a_1$ in the methanol and under the hydrogen atmosphere (the second voltammogram from the bottom in FIG. 1), an irreversible oxidation wave appeared at +173 mV (vs. Fc/Fc⁺). It is considered that the oxidation wave is assigned to the oxidation process of the hydride complex $5a_1$.

In the cyclic voltammogram of the hydride complex $5a_1$ in the methanol and under the nitrogen atmosphere (the second voltammogram from the top in FIG. 1), an irreversible oxidation wave appeared at +173 mV (vs. Fc/Fc⁺). Two small reduction waves observed in the cyclic voltammogram (at −587 mV (vs. Fc/Fc⁺) and −1180 mV (vs. Fc/Fc⁺)) are assigned to the complex $1a_1$ contained in the sample. Meanwhile, in the cyclic voltammogram of the hydride complex $5a_1$ in the methanol and under the hydrogen atmosphere (the first voltammogram from the top in FIG. 1), the current value of the oxidation wave appearing at +173 mV (vs. Fc/Fc⁺) is higher than the current value of the oxidation wave under the nitrogen atmosphere. By comparing these two cyclic voltammograms of the hydride complex $5a_1$, it was electrochemically proven that the hydride complex $5a_1$ is catalytically reactive with hydrogen.

(4) Conclusion of the Evaluation of Hydrogen Oxidation Reaction

As the result of considering the evaluation results of the above (1) to (3), the estimated reaction mechanism of the catalyst reaction is as shown in the following formula (5a). In the following formula (5a), a complex 1a (divalent cation) corresponds to the cationic moiety of the complex $1a_1$, and a complex 5a (monovalent cation) corresponds to the cationic moiety of the hydride complex $5a_1$.

As shown in the following formula (5a), by the reaction of the complex 1a with hydrogen, the complex 5a is produced with the production of one equivalent of protons. By the oxidation of the complex 5a, the complex 1a is regained with the production of another one equivalent of protons.

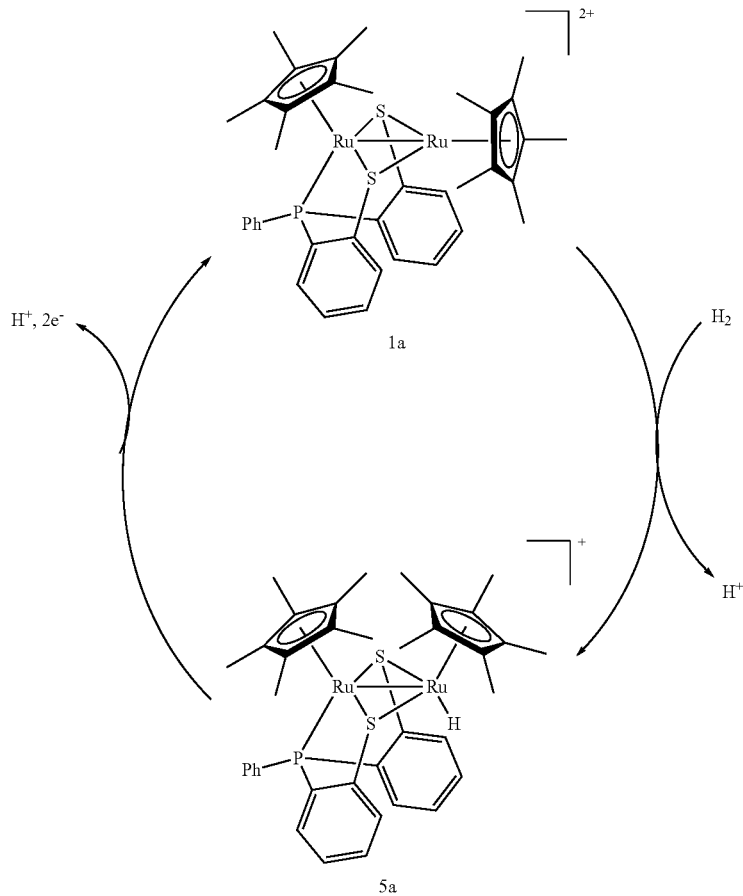

Formula (5a)

In the cyclic voltammogram of the complex $1a_1$ under the nitrogen atmosphere (the first voltammogram from the bottom in FIG. 1), an irreversible small oxidation wave is observed at +173 mV (vs. Fc/Fc⁺). This corresponds to the oxidation wave appearing at +173 mV (vs. Fc/Fc⁺) in the cyclic voltammogram of the hydride complex $5a_1$ (the first and second voltammograms from the top in FIG. 1). It is expected that the oxidation wave on the cyclic voltammogram of the complex $1a_1$ under the nitrogen atmosphere, shows that the hydride complex $5a_1$ was produced by the reaction of a two-electron reduction species in the complex 1a₁ with methanol-derived protons or a small amount of water-derived protons.

The following formula (15) shows a predictable reduction process from the complex 1a (divalent cation) to the complex 5a (monovalent cation). According to the following formula (15), the complex 1a becomes a complex 6a (two-electron reduction species) by two-electron reduction, and the complex 6a is oxidized by protons to be the complex 5a.

By the following formula (15), that the two reduction waves (at −587 mV (vs. Fc/Fc⁺) and −1180 mV (vs. Fc/Fc⁺)) in the cyclic voltammogram of the complex 1a₁ under the hydrogen atmosphere (the second voltammogram from the bottom in FIG. 1) become irreversible, can be explained. In the methanol and under the hydrogen atmosphere, the hydride complex 5a₁ is produced from the complex 1a₁, and one equivalent of protons are produced. According to the following formula (15), the two-electron reduction species of the complex 1a₁ captures a lot of the protons present in the methanol and quickly becomes the hydride complex 5a₁, accordingly. Therefore, the two-electron reduction species of the complex 1a₁ no longer exists in the electrode vicinity. As a result, it is considered that the oxidation process of the two-electron reduction species does not appear as an oxidation wave, as shown in the cyclic voltammogram of the complex 1a₁ under the hydrogen atmosphere.

Formula (15)

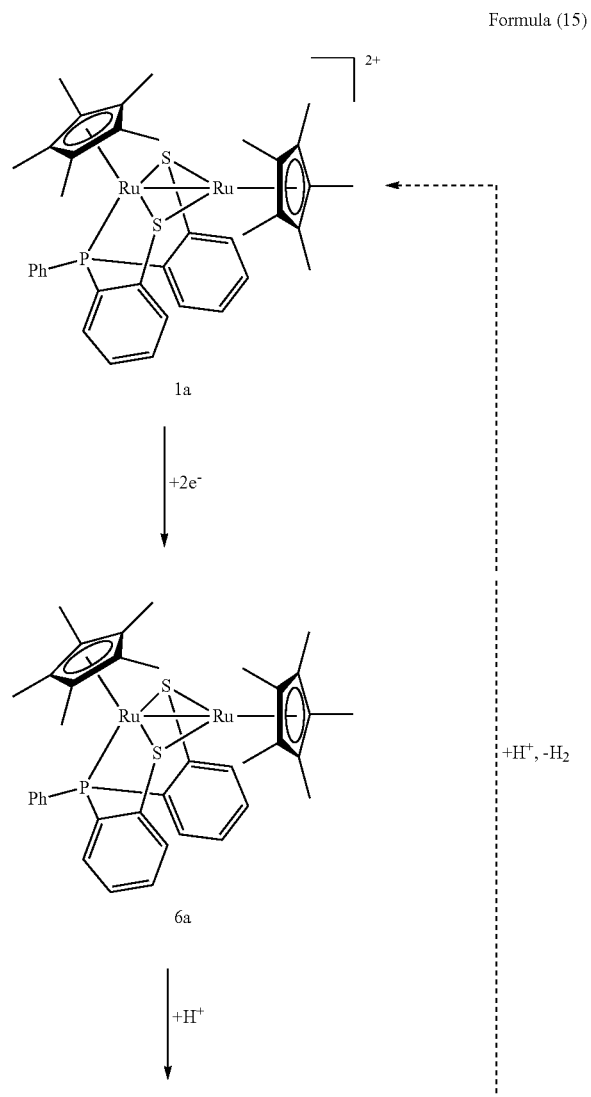

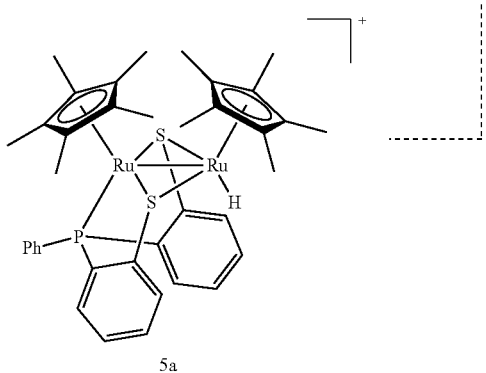

In light of both the formula (13) and the formula (15), it is considered that by the use of the hydrogen oxidation catalyst of the present invention, proton reduction reaction in which protons are catalytically reduced to remove hydrogen, is made possible.

The invention claimed is:

1. A fuel cell comprising a hydrogen oxidation catalyst, wherein the hydrogen oxidation catalyst is a dinuclear transition metal complex having a chemical structure represented by the following general formula (1) or (2):

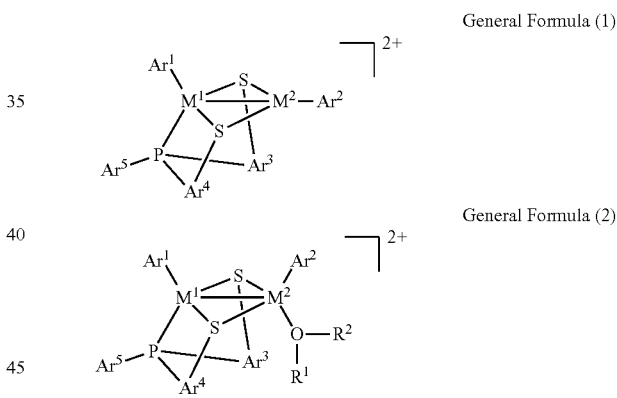

wherein, in the general formulae (1) and (2),
$M^1$ and $M^2$ are any one of the following:
(a) both $M^1$ and $M^2$ are Ru,
(b) $M^1$ is Fe and $M^2$ is Ru, and
(c) $M^1$ is Ru and $M^2$ is Fe;
$Ar^1$ and $Ar^2$ are each independently a cyclopentadienyl group or a pentamethylcyclopentadienyl group;
$Ar^3$ and $Ar^4$ are each independently a divalent aromatic hydrocarbon group having 6 to 12 carbon atoms; and $Ar^5$ is a monovalent aromatic hydrocarbon group having 6 to 12 carbon atoms, and in the general formula (2), $R^1$ and $R^2$ are each independently a hydrogen atom or a monovalent aliphatic hydrocarbon group having 1 to 3 carbon atoms.

2. The fuel cell of claim 1, further comprising hydrogen, wherein the hydrogen oxidation catalyst is an anode catalyst for the fuel cell and the hydrogen is a fuel.

* * * * *